US008409805B2

(12) United States Patent
Latham

(10) Patent No.: US 8,409,805 B2
(45) Date of Patent: Apr. 2, 2013

(54) METHOD OF AMPLIFICATION OF GC-RICH DNA TEMPLATES

(75) Inventor: Gary J. Latham, Austin, TX (US)

(73) Assignee: Asuragen, Inc., Austin, TX (US)

( * ) Notice: Subject to any disclaimer, the term of this patent is extended or adjusted under 35 U.S.C. 154(b) by 0 days.

(21) Appl. No.: 12/371,306

(22) Filed: Feb. 13, 2009

(65) Prior Publication Data

US 2010/0209970 A1 Aug. 19, 2010

(51) Int. Cl.
*C12Q 1/68* (2006.01)
*C12P 19/34* (2006.01)
*C07H 21/04* (2006.01)

(52) U.S. Cl. .................... 435/6.12; 435/91.2; 536/24.33
(58) Field of Classification Search ............. 435/6, 91.2; 536/24.33
See application file for complete search history.

(56) References Cited

U.S. PATENT DOCUMENTS

| | | | |
|---|---|---|---|
| 4,683,202 A | 7/1987 | Mullis | |
| 5,648,211 A | 7/1997 | Fraiser et al. | |
| 5,658,764 A | 8/1997 | Pergolizzi et al. | |
| 5,843,730 A | 12/1998 | Wain-Hobson et al. | |
| 5,976,842 A * | 11/1999 | Wurst | 435/91.2 |
| 6,143,504 A * | 11/2000 | Das et al. | 435/6 |
| 6,200,747 B1 | 3/2001 | Pergolizzi et al. | |
| 6,287,824 B1 | 9/2001 | Lizardi | |
| 6,326,173 B1 | 12/2001 | Edman et al. | |
| 6,335,165 B1 | 1/2002 | Navot et al. | |
| 6,410,278 B1 | 6/2002 | Notomi et al. | |
| 6,670,124 B1 * | 12/2003 | Chow et al. | 435/6 |
| 6,881,559 B2 | 4/2005 | Sobek et al. | |
| 7,030,220 B1 | 4/2006 | Ankenbauer et al. | |
| 2007/0207463 A1 * | 9/2007 | Liu et al. | 435/6 |
| 2008/0113355 A1 | 5/2008 | Hagerman et al. | |
| 2008/0124709 A1 * | 5/2008 | Huang et al. | 435/6 |
| 2008/0176293 A1 | 7/2008 | Rohayem et al. | |

FOREIGN PATENT DOCUMENTS

| | | |
|---|---|---|
| AU | 671418 | 9/1992 |
| WO | WO 92/14840 | 9/1992 |
| WO | WO 9315225 A1 * | 8/1993 |
| WO | WO 9315225 A1 | 8/1993 |
| WO | WO 0043531 | 7/2000 |
| WO | WO 2008/011170 | 1/2008 |

OTHER PUBLICATIONS

Frey, UH. et al. PCR-amplification of GC-rich regions: 'slowdown PCR'. Nature Protocols, vol. 3, No. 8, pp. 1312-1317, published online Jul. 2008.*
Kwon, SH. et al. Molecular screening for fragile X syndrome in mentally handicapped children in Korea. j Korean Med Sci., vol. 16, pp. 271-275, 2001.*
Fromant, M et al. Direct random mutagenesis of gene-sized DNA fragments using polymerase chain reaction. Analytical Biochemistry, vol. 224, pp. 347-353, 1995.*

Griep, M. et al. DNA polymerase chain reaction: a model of error frequencies and extension rates. AlChE Journal, vol. 52, No. 1, 2006.*
Tzeng, CC. et al. An effective strategy of using molecular testing to screen mentally retarded individuals for fragile X syndrome. Diagnostic Molecular Pathology, vol. 10(1), p. 34-40, 2001.*
Parida, M. et al. Loop mediated isothermal amplification (LAMP): A new generation of innovative gene amplification technique; perspcetives in clincal diagnosis of infectious diseases. Rev. Med. Virol., vol. 18 (6), p. 407-421, 2008.*
Bachinski et al., "Confirmation of the Type 2 Myotonic Dystrophy $(CCTG)_n$, Expansion Mutation in Patients with Proximal Myotonic Myopathy/Proximal Myotonic Dystrophy of Different European Origins: A Single Shared Haplotype Indicates an Ancestral Founder Effect," *Am. J. Hum. Genet.* 73:835-848 (2003).
Baskaran et al., "Uniform Amplification of a Mixture of Deoxyribonucleic Acids with Varying GC Content," *Genome Res.* 6:633-638 (1996) by Cold Spring Harbor Laboratory Press.
Blazej et al., "Microfabricated Bioprocessor for Integrated Nanoliter-Scale Sanger DNA Sequencing," *Proc. Natl. Acad. Sci. USA* 103:7240-7245 (2006).
Cadwell et al., "Randomization of Genes by PCR Mutagenesis," *PCR Methods Appl.* 2:28-33 (1992) by Cold Spring Harbor Laboratory Press.
Cagnoli et al., "Detection of Large Pathogenic Expansions in *FRDA1*, *SCA10*, and *SCA12* Genes Using a Simple Fluorescent Repeat-Primed PCR Assay," *J. Mol. Diagn.* 6:96-100 (2004).
Cagnoli et al., "Large Pathogenic Expansions in the *SCA2* and *SCA7* Genes Can Be Detected by Fluorescent Repeat-Primed Polymerase Chain Reaction Assay," *J. Mol. Diagn.* 8:128-132 (2006).
Ciotti et al., "Triplet Repeat Primed PCR (TP PCR) in Molecular Diagnostic Testing for Friedreich Ataxia," *J Mol. Diag.* 6:285-289 (2004).
Cirino et al., "Generating Mutant Libraries Using Error-Prone PCR," *Methods Mol. Biol.* 231:3-9 (2003).
Cline et al., "PCR Fidelity of *Pfu* DNA Polymerase and Other Thermostable DNA Polymerases," *Nucleic Acids Res.* 24:3546-3551 (1996).
Dean et al., "Instability in the Transmission of the Myotonic Dystrophy CTG Repeat in Human Oocytes and Preimplantation Embroyos," *Fertil. Steril.* 86:98-105 (2006).
Deiman et al., "Efficient Amplification with NASBA® of Hepatitis B Virus, Herpes Simplex Virus and Methicillin Resistant *Staphylococcus aureus* DNA," *J. Viral. Methods* 151:283-293 (2008).
Dombrowski et al., "Premutation and Intermediate-Size *FRM1* Alleles in 10 572 Males from the General Population: Loss of an AGG Interruption is a Late Event in the Generation of Fragile X Syndrome Alleles," *Hum. Mol. Genet.* 11:371-378 (2002).
Dorschner et al., "Diagnosis of Five Spinocerebellar Ataxia Disorders by Multiplex Amplification and Capillary Electrophoresis," *J. Mol. Diag.* 4:108-113 (2002).
K. Eckert and T. Kunkel, PCR: A Practical Approach (The Practical Approach Series), Oct. 10, 1991, Chapter 14, pp. 225-246, Oxford University Press.
Eichler et al., "Length of Uninterrupted CGG Repeats Determines Instability in the *FMR1* Gene," *Nat. Genet.* 8:88-94 (1994).
Fromant et al., "Direct Random Mutagenesis of Gene-Sized DNA Fragments Using Polymerase Chain Reaction," *Anal. Biochem.* 224:347-353 (1995).

(Continued)

Primary Examiner — Prabha Chunduru
(74) *Attorney, Agent, or Firm* — Finnegan, Henderson, Farabow, Garrett & Dunner, LLP

(57) ABSTRACT

Methods are provided for increasing the processivity of DNA polymerases on GC-rich templates. The methods relate to providing enhancers and biased ratios of dNTPs, and may be used in DNA amplification reactions. The methods are useful for detecting genotypes associated with GC-rich repeats, including Fragile X Syndrome.

27 Claims, 2 Drawing Sheets

OTHER PUBLICATIONS

Gecz et al., "Identification of the Genes FMR2, Associated with FRAXE Mental Retardation," *Nat. Genet.* 13:105-108 (1996).

H. Gruegelsiepe, et al., Handbook of RNA Biochemistry, May 6, 2005, Wiley-VCH, Weinheim, Germany, Chapter 1, pp. 1-21.

Gu et al., "Identification of FMR2, a Novel Gene Associated with the FRAXE CCG Repeat and CpG Island," *Nat. Genet.* 13:109-113 (1996).

Henke et al., "Betaine Improves the PCR Amplification of GC-Rich DNA Sequences," *Nucleic Acids Res.* 25:3957-3958 (1997).

Hirst et al., "Precursor Arrays for Triplet Repeat Expansion at the Fragile X Locus," *Hum. Mol. Genet.* 3:1553-1560(1994).

Innis et al., "DNA Sequencing with *Themius aquaticus* DNA Polymerase and Direct Sequencing of Polymerase Chain Reaction-Amplified DNA," *Proc. Natl. Acad. Sci. USA* 85:9436-9440 (1988).

Jama et al., "Direct PCR From Whole Blood," poster 102808 (2008) at http://www.kapabiosystems.com/public/files/pdfs/.

Klepárník et al., "Electromigration Behaviour of DNA Molecules at the Free Electrolyte-Polymer Solution Interface," *J. Chromatogr.* 772:243-253 (1997).

Kolesar et al., "Direct Quantification of AD-36 Adenovirus DNA by Capillary Electrophoresis with Laser-Induced Fluorescence", J, Chromatography B, pp. 1-8 (2000).

Kraff et al., "Screen for Excess *FMR1* Premutation Alleles Among Males with Parkinsonism," *Arch. Neurol.* 64:1002-1006 (2007).

Larsen et al., "Haplotype and AGG-Interspersion Analysis of FMR1 (CGG)n. Alleles in the Danish Population: Implications for Multiple Mutational Pathways Towards Fragile X Alleles," *Am. J. Med. Genet.* 93:99-106 (2000).

Latham et al., "Evaluation of a Novel FMR1 PCR Assay that Can Amplify Fragile X Full Mutations," abstract published at http://submissions.miracd.com/acmg (Mar. 25, 2009).

Levinson et al., "Improved Sizing of Fragile X CCG Repeats by Nested Polymerase Chain Reaction," *Am. J. Med. Genet.* 51:527-534 (1994).

Lyon et al., "A Rapid PCR Assay Suitable for Fragile X Population Screening," abstract posted on http://submissions.miracd.com/acmg on or before Mar. 19, 2009.

M. J. Mcpherson & S. G. Moller, PCR: The Basics ($2^{nd}$ Ed., Taylor & Francis) (2006), Chapter 3, pp. 23-63, Chapter 4, pp. 65-85, Chapter 7, pp. 137-183, Chapter 11, pp. 257-281.

Musso et al., "Betaine, Dimethyl Sulfoxide, and 7-Deaza-dGTP, a Powerful Mixture for Amplification of GC-Rich DNA Sequences," *J. Mol. Diagn.* 8:544-550 (2006).

Nolin et al., "Expansion of the Fragile X CGG Repeat in Famales with Premutation of Intermediate Alleles," *Am. J. Hum. Genet.* 72:454-464 (2003).

O'Connell et al., "Standardization of PCR Amplification for Fragile X Trinucleotide Repeat Measurements," *Clin. Genet.* 61:13-20 (2002).

Pembrey et al., "An Assessment of Screening Strategies for Fragile X Syndrome in the UK," *Health Technol. Assess.* 5:1-95 (2001).

Saluto et al., "An Enhanced Polymerase Chain Reaction Assay to Detect Pre- and Full Mutation Alleles of the *Fragile X Mental Retardation 1 Gene*," *J. Mol. Diagn.* 7:605-612 (2005).

Saul et al., "Fragile X Syndrome Detection in Newborns—Pilot Study," *Genet. Med.* 10:714-719 (2008).

Sermon et al., "Preimplantation Diagnosis for Fragile X Syndrome Based on the Detection of the Non-Expanded Paternal and Maternal CGG," *Prenat Diagn.* 19:1223-1230 (1999).

Sermon et al., "PGD in the Lab for Triplet Repeat Diseases—Myotonic Dystrophy, Huntington's Disease and Fragile-X Syndrome," *Mol. Cell. Endocrinol.* 183:S77-S85 (2001).

Sista et al., "Development of a Digital Microfluidic Platform for Point of Care Testing," *Lab Chip* 8:2091-2104 (2008).

Snow et al., "Sequence Analysis of the Fragile X Trinucleotide Repeat: Implications for the Origin of the Fragile X Mutation," *Hum. Mol. Genet.* 3:1543-1551 (1994).

Strom et al., "Development of a Novel, Accurate, Automated, Rapid, High-Throughput Technique Suitable for Population-Based Carrier Screening for Fragile X Syndrome," *Genetics in Medicine* 9:199-207 (2007).

Tassone et al., "A Rapid Polymerase Chain Reaction-Based Screening Method for Identification of All Expanded Alleles of the Fragile X (*FMR1*) Gene in Newborn and High-Risk Populations," *J. Mol. Diagn.* 10:43-49 (2008).

J. Vartanian, et al., "Hypermutagenic PCR involving all four transitions and a sizeable proportion of transversions," 1996, Nucleic Acids Research, vol. 24, No. 14, 2627-2631, Oxford University Press.

J. Warner, et al., "A general method for the detection of large CAG repeat expansions by fluorescent PCR," J. Med Genet, 1996, vol. 33, 1022-1026.

Wallace et al., "Fragile X Analysis: A Multi-Centre Assessment of the Abbott Molecular Fragile X Analyte Specific Reagent (ASR) Kit," *Technology Assessment Report—Abbott Molecular Fragile X ASR*, National Genetics Reference Laboratory, Manchester, UK, Jan. 2008, pp. 1-105.

Weisman-Shomer et al., "Interruption of the Fragile X Syndrome Expanded Sequence $d(CGG)_n$. By Interspersed d(AGG) Trinucleotides Diminishes the Formation and Stability of $d(CG-G)_n$Tetrahelical Structures", Nucleic Acids Res. 28:1535-41 (2000).

Wilson et al., "Random Mutagenesis by PCR," *Curr. Protoc. Molec. Biol.*, Ch. 8, Unit 8.3 (2000) pp. 8.3.1-8.3.9.

Zhong et al., "Fragile X 'Gray Zone' Alleles: AGG Patterns, Expansion, Risks, and Associated Haplotypes," *Am. J. Med. Genet.* 64:261-5 (1996).

Zhong et al., "Fragile X gene instability: anchoring AGGs and linked microsatellites," Am. J. Hum. Genet. 57:351-361 (1995).

Zhou, et at., "Robust Fragile X $(CGG)_n$ Genotype Classification Using a Methylation Specific Triple PCR Assay," *J. Med. Genet.* 41:e45 (2004), downloaded from http://www.jmg/bmj.com on Sep. 5, 2008.

Chen et al., "An Information-rich CGG repeat primed PCR that detects the full range of fragile X expanded alleles and minimizes the need for southern blot analysis", J. Mol. Diagn., 12:5, pp. 589-600, 2010.

Filipovic-Sadic et al., "A Novel FMR1 PCT Method for the Routine Detection of Low Abundance Expanded Alleles and Full Mutations in Fragile X Syndrome", Clinical Chemistry, 56:3, pp. 399-408, 2010.

Henke et al., "Betaine Improves the PCR Amplification of GC-Rich DNA Sequences", Nucleic Acids Research, 25:19, pp. 3957-3958, 1997.

International Search Report and Written Opinion for PCT/US2010/023173, dated May 20, 2010, Beatrix Tietze-Epoupa and Frank Mueller.

Kunst et al., "FMR1 in Global Populations", Am. J. Hum. Genet. 58, pp. 513-522, 1996.

Wilson et al., "Consensus Characterization of 16 FMR1 Reference Materials: A Consortium Study", Journal of Molecular Diagnostics, 10:1, pp. 2-12, 2008.

Bell et al., "Physical mapping across the fragile X: hypermethylation and clinical expression of the fragile X syndrome," *Cell* 64:861-866 (1991).

Brown et al., "Rapid fragile X carrier screening and prenatal diagnosis using a nonradioactive PCR test," *Journal of the American Medical Association*, 270:1569-1575 (1993).

Brown et al., "Prenatal diagnosis and carrier screening for fragile X by PCR," *American Journal of Medical Genetics* 64:191-195 (1996).

Cao et al., "A simple fragile X PCR assay with 7-deazaguanine-substituted DNA visualized by ethidium bromide," *Molecular and Cellular Probes* 8:177-180 (1994).

Chong et al., "Robust amplification and ethidium-visible detection of the fragile X syndrome CGG repeat using Pfu polymerase," *American Journal of Medical Genetics* 51:522-526 (1994).

Erster et al., "Polymerase chain reaction analysis of fragile X mutations," *Human Genetics* 90:55-61 (1992).

Fernandez-Carvajal et al., "Expansion of an FMR1 grey-zone allele to a full mutation in two generations," *Journal of Molecular Diagnostics* 11(4):306-310 (2009).

Fu et al., "Variation of the CGG repeat at the fragile X site results in genetic instability: resolution of the Sherman paradox," *Cell* 67:1047-1058 (1991).

Haddad et al., "A PCR-Based Test Suitable for Screening for Fragile X Syndrome Among Mentally Retarded Males," *Hum. Genet.* 97:808-812 (1996).

Hamdan et al., "Automated Detection of Trinucleotide Repeats in Fragile X Syndrome," *Molecular Diagnosis* 2:259-269 (1997).

Hecimovic et al., "A simple and rapid analysis of triplet repeat diseases by expand long PCR," *Clinical Chemistry and Lab Medicine* 39(12):1259-1262 (2001).

Houdayer et al., "Improved fluorescent PCR-based assay for sizing CGG repeats at the FRAXA locus," *Clinical Chemistry and Lab Medicine* 37(4): 397-402 (1999).

Kremer et al., "Mapping of DNA instability at the fragile X to a trinucleotide repeat sequence p(CCG)n," *Science* 252:1711-1714 (1991).

Oberle et al., "Instability of a 550-base pair DNA segment and abnormal methylation in fragile X syndrome." *Science* 252:1097-1102 (1991).

Pergolizzi et al., "Detection of full fragile X mutation," *Lancet* 339:271-272 (1992).

Verkerk et al., "Identification of a gene (FMR-1) containing a CGG repeat coincident with a breakpoint cluster region exhibiting length variation in fragile X syndrome," *Cell* 65:905-914 (1991).

Vincent et al., "Abnormal pattern detected in fragile-X patients by pulsed-field gel electrophoresis," *Nature* 349:624-626 (1991).

Wang et al., "A rapid, non-radioactive screening test for fragile X mutations at the FRAXA and FRAXE loci," *Journal of Medical Genetics* 32:170-173 (1995).

Yu et al., "Fragile X genotype characterized by an unstable region of DNA," *Science* 252:1179-1181 (1991).

PCT International Preliminary Report on Patentability and Written Opinion of the International Searching Authority for International Application No. PCT/US2010/023173, mailed Aug. 25, 2011.

* cited by examiner

SEQUENCE LISTING

```
<160> NUMBER OF SEQ ID NOS: 37

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
cggtggaggg ccgcctctga gc                                              22

<210> SEQ ID NO 2
<211> LENGTH: 25
<212> TYPE: DNA
<213> ORGANISM: Artificial Sequence
<220> FEATURE:
<223> OTHER INFORMATION: primer

<400> SEQUENCE: 2
caggcgctca gctccgtttc ggttt                                           25

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
cagtcaggcg ctcagctccg tttcg                                           25

<210> SEQ ID NO 4
<211> LENGTH: 24
<212> TYPE: DNA
<213> ORGANISM: Artificial Sequence
<220> FEATURE:
```

```
<223> OTHER INFORMATION: primer

<400> SEQUENCE: 4
tccggtggag ggccgcctct gagc                                            24

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
ggttcggcct cagtcaggcg ctcagctccg tttcg                                35

<210> SEQ ID NO 6
<211> LENGTH: 36
<212> TYPE: DNA
<213> ORGANISM: Artificial Sequence
<220> FEATURE:
<223> OTHER INFORMATION: primer

<400> SEQUENCE: 6
gggttcggcc tcagtcaggc gctcagctcc gtttcg                               36

<210> SEQ ID NO 7
<211> LENGTH: 26
<212> TYPE: DNA
<213> ORGANISM: Artificial Sequence
<220> FEATURE:
<223> OTHER INFORMATION: primer

<400> SEQUENCE: 7
gcgggccggg ggttcggcct cagtca                                          26

<210> SEQ ID NO 8
<211> LENGTH: 25
<212> TYPE: DNA
<213> ORGANISM: Artificial Sequence
<220> FEATURE:
<223> OTHER INFORMATION: primer

<400> SEQUENCE: 8
cagcgggccg ggggttcggc ctcag                                           25

<210> SEQ ID NO 9
<211> LENGTH: 25
<212> TYPE: DNA
<213> ORGANISM: Artificial Sequence
<220> FEATURE:
<223> OTHER INFORMATION: primer

<400> SEQUENCE: 9
gcagcgggcc ggggttcgg cctca                                            25

<210> SEQ ID NO 10
<211> LENGTH: 25
<212> TYPE: DNA
<213> ORGANISM: Artificial Sequence
<220> FEATURE:
<223> OTHER INFORMATION: primer

<400> SEQUENCE: 10
gggccggggg ttcggcctca gtcag                                           25

<210> SEQ ID NO 11
```

```
<211> LENGTH: 26
<212> TYPE: DNA
<213> ORGANISM: Artificial Sequence
<220> FEATURE:
<223> OTHER INFORMATION: primer

<400> SEQUENCE: 11
ggggttcggc ctcagtcagg cgctca                                        26

<210> SEQ ID NO 12
<211> LENGTH: 27
<212> TYPE: DNA
<213> ORGANISM: Artificial Sequence
<220> FEATURE:
<223> OTHER INFORMATION: primer

<400> SEQUENCE: 12
ggggttcggc ctcagtcagg cgctcag                                       27

<210> SEQ ID NO 13
<211> LENGTH: 30
<212> TYPE: DNA
<213> ORGANISM: Artificial Sequence
<220> FEATURE:
<223> OTHER INFORMATION: primer

<400> SEQUENCE: 13
ggcgctcagc tccgtttcgg tttcacttcc                                    30

<210> SEQ ID NO 14
<211> LENGTH: 28
<212> TYPE: DNA
<213> ORGANISM: Artificial Sequence
<220> FEATURE:
<223> OTHER INFORMATION: primer

<400> SEQUENCE: 14
tcaggcgctc agctccgttt cggtttca                                      28

<210> SEQ ID NO 15
<211> LENGTH: 26
<212> TYPE: DNA
<213> ORGANISM: Artificial Sequence
<220> FEATURE:
<223> OTHER INFORMATION: primer

<400> SEQUENCE: 15
cacttccggt ggagggccgc ctctga                                        26

<210> SEQ ID NO 16
<211> LENGTH: 25
<212> TYPE: DNA
<213> ORGANISM: Artificial Sequence
<220> FEATURE:
<223> OTHER INFORMATION: primer

<400> SEQUENCE: 16
ttccggtgga gggccgcctc tgagc                                         25

<210> SEQ ID NO 17
<211> LENGTH: 25
<212> TYPE: DNA
<213> ORGANISM: Artificial Sequence
<220> FEATURE:
<223> OTHER INFORMATION: primer

<400> SEQUENCE: 17
```

-continued

```
cgcacttcca ccaccagctc ctcca                                          25

<210> SEQ ID NO 18
<211> LENGTH: 21
<212> TYPE: DNA
<213> ORGANISM: Artificial Sequence
<220> FEATURE:
<223> OTHER INFORMATION: primer

<400> SEQUENCE: 18
ggagcccgcc cccgagaggt g                                              21

<210> SEQ ID NO 19
<211> LENGTH: 21
<212> TYPE: DNA
<213> ORGANISM: Artificial Sequence
<220> FEATURE:
<223> OTHER INFORMATION: primer

<400> SEQUENCE: 19
gggagcccgc ccccgagagg t                                              21

<210> SEQ ID NO 20
<211> LENGTH: 26
<212> TYPE: DNA
<213> ORGANISM: Artificial Sequence
<220> FEATURE:
<223> OTHER INFORMATION: primer

<400> SEQUENCE: 20
cgcacttcca ccaccagctc ctccat                                         26

<210> SEQ ID NO 21
<211> LENGTH: 23
<212> TYPE: DNA
<213> ORGANISM: Artificial Sequence
<220> FEATURE:
<223> OTHER INFORMATION: primer

<400> SEQUENCE: 21
cgggagcccg cccccgagag gtg                                            23

<210> SEQ ID NO 22
<211> LENGTH: 23
<212> TYPE: DNA
<213> ORGANISM: Artificial Sequence
<220> FEATURE:
<223> OTHER INFORMATION: primer

<400> SEQUENCE: 22
ccgggagccc gccccccgaga ggt                                           23

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
ccgggagccc gccccccgaga ggtg                                          24

<210> SEQ ID NO 24
<211> LENGTH: 26
<212> TYPE: DNA
<213> ORGANISM: Artificial Sequence
<220> FEATURE:
```

<223> OTHER INFORMATION: primer

<400> SEQUENCE: 24
cgccgggagc ccgcccccga gaggtg                                          26

<210> SEQ ID NO 25
<211> LENGTH: 26
<212> TYPE: DNA
<213> ORGANISM: Artificial Sequence
<220> FEATURE:
<223> OTHER INFORMATION: primer

<400> SEQUENCE: 25
gcgccgggag cccgccccg agaggt                                           26

<210> SEQ ID NO 26
<211> LENGTH: 25
<212> TYPE: DNA
<213> ORGANISM: Artificial Sequence
<220> FEATURE:
<223> OTHER INFORMATION: primer

<400> SEQUENCE: 26
cgccgggagc ccgcccccga gaggt                                           25

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
gcgccattgg agccccgcac ttccacca                                        28

<210> SEQ ID NO 28
<211> LENGTH: 25
<212> TYPE: DNA
<213> ORGANISM: Artificial Sequence
<220> FEATURE:
<223> OTHER INFORMATION: primer

<400> SEQUENCE: 28
gcgccattgg agccccgcac ttcca                                           25

<210> SEQ ID NO 29
<211> LENGTH: 25
<212> TYPE: DNA
<213> ORGANISM: Artificial Sequence
<220> FEATURE:
<223> OTHER INFORMATION: primer

<400> SEQUENCE: 29
agcgccattg gagccccgca cttcc                                           25

<210> SEQ ID NO 30
<211> LENGTH: 25
<212> TYPE: DNA
<213> ORGANISM: Artificial Sequence
<220> FEATURE:
<223> OTHER INFORMATION: primer

<400> SEQUENCE: 30
cgccattgga gccccgcact tccac                                           25

<210> SEQ ID NO 31

```
<211> LENGTH: 25
<212> TYPE: DNA
<213> ORGANISM: Artificial Sequence
<220> FEATURE:
<223> OTHER INFORMATION: primer

<400> SEQUENCE: 31
ttggagcccc gcacttccac cacca                                    25

<210> SEQ ID NO 32
<211> LENGTH: 28
<212> TYPE: DNA
<213> ORGANISM: Artificial Sequence
<220> FEATURE:
<223> OTHER INFORMATION: primer

<400> SEQUENCE: 32
agccccgcac ttccaccacc agctcctc                                 28

<210> SEQ ID NO 33
<211> LENGTH: 28
<212> TYPE: DNA
<213> ORGANISM: Artificial Sequence
<220> FEATURE:
<223> OTHER INFORMATION: primer

<400> SEQUENCE: 33
gagccccgca cttccaccac cagctcct                                 28

<210> SEQ ID NO 34
<211> LENGTH: 28
<212> TYPE: DNA
<213> ORGANISM: Artificial Sequence
<220> FEATURE:
<223> OTHER INFORMATION: primer

<400> SEQUENCE: 34
cattggagcc ccgcacttcc accaccag                                 28

<210> SEQ ID NO 35
<211> LENGTH: 30
<212> TYPE: DNA
<213> ORGANISM: Artificial Sequence
<220> FEATURE:
<223> OTHER INFORMATION: primer

<400> SEQUENCE: 35
cccgcacttc caccaccagc tcctccatct                               30

<210> SEQ ID NO 36
<211> LENGTH: 30
<212> TYPE: DNA
<213> ORGANISM: Artificial Sequence
<220> FEATURE:
<223> OTHER INFORMATION: primer

<400> SEQUENCE: 36
tagaaagcgc cattggagcc ccgcacttcc                               30

<210> SEQ ID NO 37
<211> LENGTH: 26
<212> TYPE: DNA
<213> ORGANISM: Artificial Sequence
<220> FEATURE:
<223> OTHER INFORMATION: primer
```

```
<400> SEQUENCE: 37
aagcgccatt ggagcccgc acttcc                                                  26
```

METHOD OF AMPLIFICATION OF GC-RICH DNA TEMPLATES

This invention is in the field of DNA synthesis, particularly relating to synthesis involving GC-rich templates and products.

Since the first isolation of a DNA polymerase and determination of conditions under which DNA can be synthesized in vitro, DNA synthesis reactions have been widely used for preparative and analytical purposes in biotechnological, medical, and research applications. Polymerase chain reaction, or PCR, is a type of DNA synthesis reaction by which a DNA sequence can be amplified rapidly and exponentially. Like other cycled synthesis reactions, it involves repeatedly copying the target sequence in a cyclic manner. A typical implementation of PCR involves providing primers complementary to the ends of the desired sequence, a suitable buffer, a magnesium salt, deoxynucleotide triphosphates (dNTPs), and a thermophilic DNA polymerase. The template or target DNA, contained, for example, within a sample of genomic DNA, is exposed to these components in aqueous solution. The mixture is cycled through steps at different temperatures which promote denaturation of the template, annealing of the primers to the template, and then extension of the primers by the polymerase, creating more product. Since the product of each cycle is available as template in subsequent reactions, the amount of product increases roughly exponentially until other reaction components (initially present in excess) are depleted. See, e.g., U.S. Pat. No. 4,683,202; M. J. McPherson & S. G. Moller, *PCR: The Basics* (2$^{nd}$. Ed., Taylor & Francis) (2006).

PCR, along with other forms of cycled nucleic acid synthesis reactions, is a standard tool in molecular biology, biotechnology, and, increasingly, in medicine. Key advantages of PCR and related techniques are rapidity, low cost, sensitivity, amenability to high throughput analysis, and versatility. Amplifications require only a few hours or less, small individual reactions may consume well less than a dollar's worth in reagents, the amount of template required is typically in the nanogram range, automation can result in running thousands of reactions per day per robot, and primers can be designed to amplify almost any sequence.

PCR and related techniques are widely adopted for both analytical and preparative applications. A typical preparative application of PCR is to amplify a sequence so that it may be cloned in a heterologous vector. A specialized variant of this application is mutagenic PCR, in which the fidelity of the reaction is deliberately reduced in order to generate copies of the target sequence containing mutations. The cloned mutant copies may then be used in downstream research or experimentation. Mutagenic PCR may be accomplished by the use of biased dNTP pools, wherein dATP, dCTP, dGTP, and dTTP are not present in equimolar ratios. This may increase the frequency of incorporation of mismatches during the extension step of the PCR cycle, resulting in mutant product. See, e.g., *PCR Methods Appl.* 2: 28-33 (1992); *Anal Biochem* 224:347-353 (1995).

Although unbalanced dNTP pools have been used in the deliberately error-prone PCR described above, the mutagenic effects of such an imbalance are disfavored in other applications. Mutagenesis is disadvantageous in analytical applications generally and in preparative applications in which mutant product is not the goal. Indeed, the general undesirability of mutant product has inspired efforts to characterize and increase the fidelity of reactions such as PCR by modifying the polymerase or other reaction components. See, e.g., *Nucleic Acids Research,* 24:3546-3551 (1996); U.S. Pat. No. 7,030,220; U.S. Pat. No. 6,881,559. Moreover, the increased error rate associated with unbalanced dNTP pools would be expected to limit reaction yield, since mismatches reduce both the processivity and the incorporation rate of DNA polymerases.

A notable analytical application of PCR is in diagnosis of conditions or determinations of genotypes involving genetic loci with size polymorphisms.

An example of a locus exhibiting medically relevant size polymorphism is the 5' untranslated region (UTR) of the human FMR1 gene on the X chromosome. Normal individuals typically have 5-44 CGG repeats in this region. In contrast, alleles of this locus containing 200 to 2000 or more CGG repeats are indicative of Fragile X syndrome (FXS). Such alleles are referred to as Full Mutation alleles. These alleles are genetically unstable. Individuals with FXS may have various combinations of symptoms such as ataxia, premature ovarian failure, learning disabilities, and other cognitive/behavioral conditions, including autism-like symptoms.

One unfortunate exception to the versatility of PCR is in the difficulty of amplifying long runs of highly GC-rich sequence, including Full Mutation alleles of the FMR1 5'UTR. Attempts to optimize FMR1 PCR have included modifications to conventional PCR assay conditions. See Genome Res. 1996 July; 6(7):633-8; Nucleic Acids Res. 1997 Oct. 1; 25(19):3957-8; J. Mol. Diagn. Nov. 1, 2006 8:544-550; Am J Med Genet. 1994 Jul. 15; 51(4):527-34. Yet after more than 15 years of FMR1 PCR assay development, as recently as 2008 (Genet Med. 2008 October; 10(10):714-9) a published pilot screening study to detect Fragile X in newborns reported that "two methods of quantitative polymerase chain reaction (PCR) analysis . . . used in the in-house validation process to determine the FMR1 repeat number in females failed to produce reliable and reproducible results," and, further, that "a second [PCR] failure from either the first or secondary isolation was highly suggestive of an abnormal FMR1 CGG repeat size." (Emphasis added.) Thus, those knowledgeable in the art continue to regard reproducible PCR amplification of full mutation Fragile X alleles as an unsolved problem.

Precise evaluation of triplet repeat length by PCR has been reported up to about 100 CGG repeats, well below the size of Full Mutation alleles. Moreover, detection of any band at all becomes progressively fainter beginning at about 100 repeats. *J Mol Diagn* 7:605-12 (2005). This difficulty, combined with the heterogeneous nature of FXS symptoms, has resulted in the use of procedures such as Southern blotting in order to detect Full Mutation alleles. Id. Southern blotting is more time-consuming and costly, and much less amenable to high-throughput implementations, than PCR.

This invention is based in part on the surprising discovery that providing a biased dNTP pool results in significant improvements relative to methods known in the art in the processivity of DNA polymerases on GC-rich templates.

In certain embodiments, the application provides methods of increasing the processivity of one or more DNA polymerases on at least one GC-rich DNA template, the method comprising performing a DNA amplification reaction in an aqueous solution comprising dNTPs in a GC/AT ratio greater than one.

In other embodiments, the application provides methods that comprise amplifying the GC-rich template by PCR in an aqueous solution comprising (a) dNTPs in a GC/AT ratio between 2 and 10 and at total concentration of 0.7-0.9 mM; (b) at least one enhancer chosen from betaine, DMSO, and TWEEN-20; and (c) magnesium at a total concentration of 1.5-2 mM, wherein the at least one GC-rich template comprises CGG repeats of the 5' UTR of FMR1.

And in another embodiment, the application provides method of detecting a genotype associated with a GC-rich trinucleotide repeat disorder such as Fragile X Syndrome, Fragile X-associated tremor ataxia syndrome, and/or Fragile X-associated primary ovarian insufficiency, comprising performing a DNA amplification reaction on at least one GC-rich DNA template, in which the processivity of one or more DNA polymerases is increased by providing an aqueous solution comprising dNTPs in a GC/AT ratio greater than one.

DETAILED DESCRIPTION OF THE EMBODIMENTS

Figure 1:
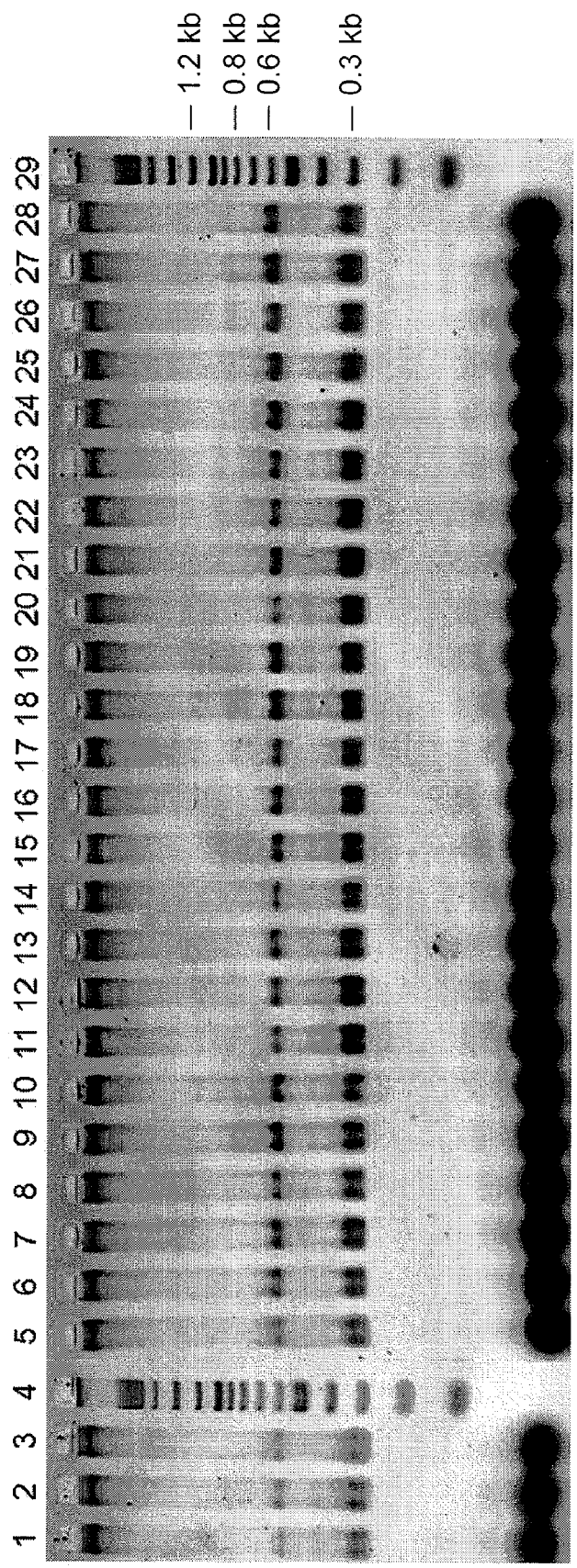
FIG. 1 is a photograph of a SYBR-Gold stained gel. Lanes 4 and 29 are size markers, and sizes of selected bands are indicated to the right of lane 29. All PCR reactions used a mixture of templates containing alleles with 20, 28-29, 118, 198, and about 330 CGG repeats in the FMR1 5' UTR. Lanes 1-3 and 5-28 show products of reactions run with various levels of GC/AT ratio, betaine concentration, and total dNTP concentration.

The invention relates to methods for synthesis of DNA in aqueous solutions wherein the template has a high level of GC richness and dNTPs are provided in a GC/AT ratio greater than one. More specifically, this invention relates to improving polymerase processivity by altering the GC/AT ratio of dNTPs in the reaction. The methods of this invention are particularly relevant to synthesis reactions such as PCR, which may be used in diagnostic applications involving loci that may be highly GC-rich, such as near the Fragile X Syndrome-associated FMR1 gene.

An "enhancer" is a chemical or composition that improves one or more aspects of performance, such as processivity, of a DNA polymerase and/or a DNA synthesis reaction.

"GC/AT Ratio" means the ratio of the concentration of the sum of dCTP, dGTP, and all nucleotide analogs thereof, to the concentration of the sum of dATP, dTTP, dUTP, and all nucleotide analogs thereof, in a given solution or mixture.

"dNTP" stands for deoxynucleotide triphosphate and refers to dATP, dCTP, dGTP, dTTP, dUTP, and analogs thereof.

"Nucleotide analogs" are molecules or ions comprising a base moiety other than the natural bases adenine (A), cytosine (C), guanine (G), thymine (T), or uracil (U), a sugar moiety identical or similar to deoxyribose, and at least one phosphate or multiple phosphate (e.g., diphosphate or triphosphate) moiety. The nucleotide analog is an analog of a specific nucleotide, in particular dATP, dCTP, dGTP, dTTP, or dUTP, when it comprises a triphosphate and a sugar moiety, the structure and configuration of both of which are suitable for incorporation into a nucleic acid double helix by a polymerase, and a base whose base pairing properties in a nucleic acid double helix and loci of incorporation by DNA polymerases in a nucleic acid double helix are most similar to one of the five previously listed nucleotides, with the exception that analogs of dTTP will generally also be analogs of dUTP and vice versa.

The term "analog" used in conjunction with terms including but not limited to "nucleoside", "base", "nucleobase", or "residue" is to be interpreted in the same manner as if it were used in conjunction with "nucleotide."

"PCR" is a DNA synthesis reaction in which the reaction mixture is subjected to at least two complete reaction cycles, each reaction cycle comprising a denaturation period and at least one annealing and/or extension period, resulting if successful in synthesis of copies of a nucleic acid template in at least the initial cycles, and copies of the copies in at least the later cycles, generally resulting in geometric amplification of the template.

"DNA" is deoxyribonucleic acid, a biopolymeric chain of predominantly deoxyribonucleotide redisues linked generally by phosphodiester bonds.

"Betaine" refers to N,N,N-trimethylglycine.

A "betaine analog" is any neutral chemical compound with a positively charged cationic functional group which bears no hydrogen atom, for example, an ammonium ion or phosphonium ion, and with a negatively charged functional group such as a carboxylate group which may not be adjacent to the cationic site. The invention may relate to the use of betaine analogs with molecular weights less than or equal to 600 Da; less than or equal to 300 Da; between 75 and 600 Da; or between 75 and 300 Da. The invention may additionally or alternatively relate to the use of betaine analogs that comprise an ammonium moiety and/or a carboxylate moiety.

"Tm" is the temperature at which 50% by mass of a given DNA sample or primer-template complex in a given solution is single-stranded, and 50% by mass is double-stranded.

"TWEEN-20" is polyethylene glycol sorbitan monolaurate, the chemical designated by CAS number 9005-64-5.

"GC-richness" is the fraction or percentage of total nucleobase residues in a nucleic acid that are guanine residues, cytosine residues, or analogs thereof. For example, a 100 nt nucleic acid that contains exactly 30 cytosines, exactly 30 guanines, exactly one cytosine analog, and exactly one guanine analog has a GC richness of 62%. In some embodiments, a GC-rich template may contain at least 51, 55, 60, 65, 70, 75, 80, 85, 90, 95, 96, 97, 98, 99, or 99.5% guanine residues, cytosine residues, or analogs thereof.

"Processivity" is the ability of a DNA Polymerase to synthesize complete copies of a template in a given reaction. Increased processivity may result in increased product yield and/or increased product size, the latter being particularly relevant for reactions involving templates for which a lower level of processivity results in a low level of synthesis of complete copies.

A. DNA Template

A DNA template is a sequence of DNA present in a sample that is the target of synthesis in a reaction catalyzed by a DNA polymerase. The GC-richness of the DNA template may be greater than or equal to 60, 65, 70, 75, 80, 85, 90, 95, 96, 97, 98, 99, or 99.5% C and G residues. The DNA template may comprise di-, tri-, or tetranucleotide repeats comprising C and G residues. The DNA template may be within or near a disease-associated locus. The DNA template may comprise at least part of the 5' UTR of the FMR1 gene. The DNA template may comprise CGG repeats of the 5' UTR of the FMR1 gene. The size of the DNA template may be about 50, 100, 200, 300, 500, or 700 bp, or 1, 1.5, 2, 2.5, 3, 4, 5, 7, or 10 kb. The size of the DNA template may be between 50 bp and 10 kb, 100 bp and 10 kb, 200 bp and 10 kb, 300 bp and 10 kb, 500 bp and 10 kb, 700 bp and 10 kb, 1 kb and 10 kb, 1.5 bp and 10 kb, 2 bp and 10 kb, 3 bp and 10 kb, 50 bp and 7 kb, 50 bp and 5 kb, 50 bp and 4 kb, 50 bp and 3 kb, 50 bp and 2 kb, 50 bp and 1.5 kb, 100 bp and 7 kb, 200 bp and 5 kb, or 300 bp and 4 kb.

B. GC/AT Ratio and Concentration of dNTPs

The invention relates to methods comprising providing dNTPs in a GC/AT Ratio greater than one and at a total dNTP concentration conducive to synthesis of DNA using GC-rich templates. The GC/AT ratio may be about 1.1, 1.2, 1.4, 1.6, 2, 2.5, 3, 4, 5, 6, 7, 8, 9, 10, 11, 12, 13, 14, 15, 16, 17, 18, 19, 20, 25, or higher. The GC/AT ratio may be between 1.1 and 20, 1.1 and 15, 1.1 and 10, 1.1 and 8, 1 and 15, 1.1 and 7, 1.1 and 6, 1.1 and 5, 1.2 and 25, 1.4 and 25, 1.6 and 25, 2 and 25, 3 and 25, 4 and 25, 5 and 25, 2 and 15, 2.5 and 10, or 4 and 10. The total dNTP concentration may be about 0.4, 0.5, 0.6, 0.7, 0.8, 0.9, 1, 1.2, 1.5, 2, or 3 mM. The dNTP concentration may be between 0.4 and 3 mM, 0.5 and 3 mM, 0.6 and 3 mM, 0.7 and 3 mM, 0.8 and 3 mM, 0.9 and 3 mM, 1 and 3 mM, 0.4 and 2 mM, 0.4 and 1.5 mM, 0.4 and 1.2 mM, 0.4 and 1 mM, 0.4 and 0.9 mM, 0.4 and 0.8 mM, 0.4 and 0.7 mM, 0.5 and 2 mM, 0.5 and 1 mM, or 0.6 and 0.9 mM.

C. Processivity, Yield and Product Size

In some embodiments, the invention provides improved processivity for a given polymerase with a given GC-rich template relative to methods known in the art. The improvements are obtained through steps comprising providing dNTPs in a GC/AT ratio greater than one. The extent of improvement may be such that the improved reaction may be capable of generating detectable products comprising about 25, 50, 100, 200, 300, 400, 500, 600, 700, 800, 900, 1000, 2000 or more CGG repeats than methods known in the art.

D. DNA Polymerase

The invention relates to methods comprising providing at least one DNA polymerase to synthesize DNA from dNTPs in a template dependent manner. The DNA polymerase may comprise a wild-type, modified, thermophilic, chimeric, engineered, and/or a mixture of more than one polymerase. The DNA polymerase may comprise Exact Polymerase (5 PRIME GmbH), AccuSure™ DNA Polymerase (Bioline), Phusion™ AccuPrime™ Pfx (Invitrogen), Platinum Taq DNA Polymerase High Fidelity (Invitrogen), Phire™ Hot Start DNA Polymerase (New England Biolabs), Phusion$^a$ Hot Start High-Fidelity DNA Polymerase (New England Biolabs), JumpStart™ REDTaq™ DNA Polymerase (Sigma-Aldrich), PfuUltra™ Hotstart DNA Polymerase (Stratagene), PfuTurbo® Cx Hotstart DNA Polymerase (Stratagene), PrimeSTAR™ HS DNA Polymerase (Takara), Extensor Hi-Fidelity PCR Enzyme (ABgene), ACCUZYME™ DNA Polymerase (Bioline), SAHARA™ DNA Polymerase (Bioline), VELOCITY DNA Polymerase (Bioline), GeneChoice® AccuPOL™ DNA Polymerase (GeneChoice, Inc.), GeneChoice® UniPOL™ DNA Polymerase (GeneChoice, Inc.), Elongase Enzyme Mix (Invitrogen), Pfx50™ DNA Polymerase (Invitrogen), Phusion DNA Polymerase (New England Biolabs), KOD HiFi DNA Polymerase (Novagen), KOD XL DNA Polymerase (Novagen), Expand 20 kb PLUS Thermostable DNA polymerase mixture (Roche Applied Science), Expand High Fidelity PLUS Thermostable DNA polymerase mixture (Roche Applied Science), Expand High Fidelity Thermostable DNA polymerase mixture (Roche Applied Science), Expand Long Template Thermostable DNA polymerase mixture (Roche Applied Science), Easy-A™ High-Fidelity PCR Cloning Enzyme (Stratagene), EXL™ DNA Polymerase (Stratagene), Herculase® Enhanced DNA Polymerase (Stratagene), Herculase® II Fusion DNA Polymerase (Stratagene), Kapa LongRange™ DNA Polymerase (Kapa Biosystems), Kapa HiFi™ DNA Polymerase (Kapa Biosystems), Kapa2G™ Robust DNA Polymerase (Kapa Biosystems), Kapa2G™ Robust HotStart DNA Polymerase (Kapa Biosystems), Kapa2G™ Fast DNA Polymerase (Kapa Biosystems), Kapa2G™ Fast HotStart DNA Polymerase (Kapa Biosystems), LA TAQ DNA Polymerase (Takara), Optimase DNA Polymerase (Transgenomic, Inc.), Exo-Pfu DNA Polymerase (Stratagene), HotMaster Taq DNA Polymerase (5 PRIME GmbH), HotTaq DNA Polymerase (Abnova Corporation), AmpliTaq Gold® DNA Polymerase (Applied Biosystems), Bst DNA Polymerase Lg Frag (New England Biolabs), MasterAmp™ Tfl DNA Polymerase (EPICENTRE Biotechnologies), Red Hot DNA Polymerase (ABgene), Thermoprime Plus DNA Polymerase (ABgene), Taq-red DNA Polymerase (AppliChem GmbH), BIO-X-ACT™ Long DNA Polymerase (Bioline), BIO-X-ACT™ Short DNA Polymerase (Bioline), Bioline HybriPol™ DNA Polymerase (Bioline), BioTherm Taq DNA Polymerase (eEnzyme LLC), EU-Taq DNA Polymerase (eEnzyme LLC), Synergy Taq DNA Polymerase (eEnzyme LLC), GeneChoice® RedPOL™ DNA Polymerase (GeneChoice, Inc.), AccuPrime™ GC-Rich DNA Polymerase (Invitrogen), PyroPhage® 3173 DNA Polymerase, Exo Minus (Lucigen), 9 Degrees North (Modified) DNA Polymerase (New England Biolabs), Therminator DNA Polymerase (New England Biolabs), Pwo DNA Polymerase (Roche Applied Science), Paq5000™ DNA Polymerase (Stratagene), YieldAce™ DNA Polymerase (Stratagene), e2TAK™ DNA Polymerase (Takara), or naturally occurring DNA polymerases from *P. kodakaraensis, P. furiosus, T. gorgonarius, T. zilligii, T. litoralis* "Vent™", *P.* GB-D "Deep Vent", *T.* 9N-7, *T. aggregans, T. barossii, T. fumicolans, T. celer, Pyrococcus* sp. strain ST700, *T. pacificus, P. abysii, T. profundus, T. siculi, T. hydrothermalis, Thermococcus* sp. strain GE8, *T. thioreducens, P. horikoshii* or *T. onnurineus* NA1, *Thermococcus* sp. 9°N-7, *Thermococcus* sp. GI-J, *Thermococcus* sp. MAR-13, *Thermococcus* sp. GB-C, *Thermococcus* sp. GI-H, *Thermus aquaticus, Thermus thermophilus, Thermus caldophilus, Thermus filiformis, Thermus flavus, Thermotoga maritima, Bacillus stearothermophilus*, or *Bacillus caldotenax*.

E. Nucleic Acid Amplification, PCR

The invention relates to reactions that amplify nucleic acids. Examples of amplification reactions include, without limitation, PCR, NASBA (nucleic acid sequence based amplification), SDA (strand displacement amplification), LAMP (loop-mediated isothermal amplification), and RCA (rolling circle amplification). See, e.g., U.S. Pat. No. 4,683, 202 (PCR); U.S. Pat. No. 6,326,173 and *Journal of Virological Methods* 151:283-293 (2008) (NASBA); U.S. Pat. No. 5,648,211 (SDA); U.S. Pat. No. 6,410,278 (LAMP); and U.S. Pat. No. 6,287,824 (RCA). All of the foregoing are incorporated herein by reference. The skilled artisan will understand what reagents are appropriate to provide. Each of these methods involves DNA synthesis, and as such involves the use of DNA Polymerases, nucleotides, and divalent cations (supplied as a salt), particularly magnesium, in a solution conducive to DNA polymerization and in which the template is present. The methods vary in terms of providing additional catalytic activities, the use of thermocycling or isothermal incubation, and the use and structure of primers. A buffer at a suitable pH such as between 7 and 8, between 6.5 and 8.5, between 6 and 9, or about 7.4 or 7.5 is also typically provided.

In PCR, a pair of primers are provided that bind at each end of a target region, on opposite strands such that they each prime synthesis toward the other primer. The reaction is thermocycled so as to drive denaturation of the substrate in a high temperature step, annealing of the primers at a lower temperature step, and extension at a temperature which may be but is not necessarily higher than that of the annealing step. Amplification occurs because the products of one cycle can serve as template in the next cycle.

In NASBA, an RNA polymerase (RNAP) is provided in addition to the DNA polymerase, which may also be a reverse transcriptase (RT) (e.g., an enzyme that can catalyze DNA synthesis using either an RNA or DNA template). Primers are provided that are similar to those used in PCR except that at least one primer additionally comprises a promoter sequence that is recognized by the RNAP. Thus, the product of the RT serves as template for the RNAP, which synthesizes RNA that serves as template for the RT, leading to amplification. In some forms of NASBA, RNase H is provided to produce single-stranded DNA after synthesis of an RNA-DNA hybrid by RT. Amplification occurs via the combined action of the RT and RNAP, in the absence of repeated thermal denaturation.

SDA is a technique in which DNA is amplified in an isothermal and asynchronous manner, meaning that cyclic thermal denaturation is not used to separate the strands; instead, strand displacement occurs through DNA synthesis itself, wherein extension of a 3' OH causes displacement of the downstream strand. The 3' OH is provided initially by an exterior primer and subsequently by a nicking reaction. Two pairs of primers are provided. One 'interior' pair binds surrounding the amplicon and additionally comprises 5' flaps containing a restriction site. The other, 'exterior' pair is positioned distally, i.e., further from the target region. An interior primer may bind the template, be extended, and then be displaced by synthesis from the corresponding exterior primer. Subsequently, the displaced DNA is made double-stranded, e.g., by second strand synthesis. The next step is to nick one strand of the double stranded molecule, which may be done by using modified nucleotides and a restriction site wherein the cleavage site is inactivated on one strand (but not the other) by the modified nucleotide. The restriction enzyme corresponding to this site is provided in the reaction and generates the nick. The 3' OH at the resulting nick is then extended by the DNA polymerase, displacing one strand (which may again serve as a template[1]) and the regenerated double strand molecule is again a substrate for nicking followed by extension and displacement, leading to amplification. Repeated thermal denaturation is not necessary.

[1] Note that some displaced strands will not initially be full-length but will lack the complement of the distal portion of the interior primer flap, as a consequence of the nicking. This does not impair primer binding (recall that the non-flap portion of the primer has sufficient length to anneal stably) and, upon primer binding, a 5' overhang is generated that the polymerase is able to fill in.

LAMP is an amplification procedure designed to be highly specific, that is, it can discriminate between templates differing by only a single nucleotide polymorphism (SNP), in that one allele is a substrate for amplification and the other is not. It is also isothermal. As in SDA, two pairs of primers, interior and exterior, are provided; the interior primers also have a 5' flap. However, in LAMP, the 5' flap of each interior primer contains a sequence matching a sequence within the template strand to which it binds, interior to the site where the 3' portion of the primer binds. For example, if the primer anneals to the (+) strand of a template molecule, which contains the downstream sequence A, then the primer flap may also contain sequence A. Notably, the SNP locus which is to be discriminated by this reaction is located at the edge of the region bound by the flap, corresponding to the last base at the 5' end of the flap. The last base at the 5' end of the reverse interior primer flap also corresponds to the SNP locus. As in SDA, the interior primer is extended and then displaced by extension of the exterior primer. When this occurs, the 5' flap forms a loop by binding its complement (which is now part of the same molecule; continuing the above example, the displaced strand contains the reverse complement of sequence A, designated sequence T, and the sequence A in the flap binds intramolecularly to sequence T). The reverse interior primer anneals to the looped displaced strand, interior to its 3' end (which corresponds to the reverse exterior primer) and primes synthesis, which displaces the loop and forms a partially double-stranded, partially single stranded DNA. Then, a reverse exterior primer anneals to the single stranded portion and primes synthesis, causing strand displacement. The displaced strand can now form a loop wherein its 3' end is paired to an internal portion of the molecule. Only if the SNP locus matches the 3' end (which is derived from an interior primer flap that was exogenously supplied) does extension occur. Further primer annealing, looping, and extension/displacement events, described in the reference cited above, result in selective amplification of templates with the SNP allele matching the primer flap.

In RCA, a circular DNA template is used. A primer anneals to the circle and is extended continuously, with the polymerase displacing the DNA synthesized during the previous revolution as it proceeds. This reaction proceeds with linear kinetics and produces long, concatemerized products. In double-primed RCA, a second primer is provided that anneals to the concatemerized product of the above reaction. This version of the reaction allows use of product as template, and therefore results in exponential kinetics. As in other isothermal reactions, product is made suitable for annealing to primer in double-primed RCA through strand displacement due to extension of upstream primers; in this case the primers are bound to other concatemers further upstream in the template strand.

One embodiment of the invention, for example, is to amplify a GC-rich template DNA by PCR in which dNTPs are provided with a GC/AT ratio greater than one. In cycled amplification reactions such as, for example, PCR, the number of reaction cycles may be between 20 and 40, for example, about 20, 25, 30, 35, or 40 cycles. The invention additionally relates to other amplification reactions in which a GC-rich template is amplified in a reaction in which dNTPs are provided with a GC/AT ratio greater than one; the reaction may be, for example, NASBA, SDA, LAMP, or RCA.

F. PCR Primers

The invention relates to methods comprising providing forward and reverse primers. The primers may be designed to anneal to the about 15-30, 15-25, 15-20, 20-30, or 20-25 nucleotides at each end of the template sequence.

The primers may anneal to sequences flanking the CGG repeat region in the FMR1 5' UTR. Examples of such forward primers include CGG TGG AGG GCC GCC TCT GAG C (SEQ ID NO: 1), CAG GCG CTC AGC TCC GTT TCG GTT T (SEQ ID NO: 2), CAG TCA GGC GCT CAG CTC CGT TTC G (SEQ ID NO: 3), TCC GGT GGA GGG CCG CCT CTG AGC (SEQ ID NO: 4), GGT TCG GCC TCA GTC AGG CGC TCA GCT CCG TTT CG (SEQ ID NO: 5), GGG TTC GGC CTC AGT CAG GCG CTC AGC TCC GTT TCG (SEQ ID NO: 6), GCG GGC CGG GGG TTC GGC CTC AGT CA (SEQ ID NO: 7), CAG CGG GCC GGG GGT TCG GCC TCA G (SEQ ID NO: 8), GCA GCG GGC CGG GGG TTC GGC CTC A (SEQ ID NO: 9), GGG CCG GGG GTT CGG CCT CAG TCA G (SEQ ID NO: 10), GGG GTT CGG CCT CAG TCA GGC GCT CA (SEQ ID NO: 11), GGG GTT CGG CCT CAG TCA GGC GCT CAG (SEQ ID NO: 12), GGC GCT CAG CTC CGT TTC GGT TTC ACT TCC (SEQ ID NO: 13), TCA GGC GCT CAG CTC CGT TTC GGT TTC A (SEQ ID NO: 14), CAC TTC CGG TGG AGG GCC GCC TCT GA (SEQ ID NO: 15), and TTC CGG TGG AGG GCC GCC TCT GAG C (SEQ ID NO: 16). Examples of such reverse primers include CGC ACT TCC ACC ACC AGC TCC TCC A (SEQ ID NO: 17), GGA GCC CGC CCC CGA GAG GTG (SEQ ID NO: 18), GGG AGC CCG CCC CCG AGA GGT (SEQ ID NO: 19), CGC ACT TCC ACC ACC AGC TCC TCC AT (SEQ ID NO: 20), CGG GAG CCC GCC CCC GAG AGG TG (SEQ ID NO: 21), CCG GGA GCC CGC CCC CGA GAG GT (SEQ ID NO: 22), CCG GGA GCC CGC CCC CGA GAG GTG (SEQ ID NO: 23), CGC CGG GAG CCC GCC CCC GAG AGG TG (SEQ ID NO: 24), GCG CCG GGA GCC CGC CCC CGA GAG GT (SEQ ID NO: 25), CGC CGG GAG CCC GCC CCC GAG AGG T (SEQ ID NO: 26), GCG CCA TTG GAG CCC CGC ACT TCC ACC A (SEQ ID NO: 27), GCG CCA TTG GAG CCC CGC ACT TCC A (SEQ ID NO: 28), AGC GCC ATT GGA GCC CCG CAC TTC C (SEQ ID NO: 29), CGC CAT TGG AGC CCC GCA CTT CCA C (SEQ ID NO: 30), TTG GAG CCC CGC ACT TCC ACC ACC A (SEQ ID NO: 31), AGC CCC GCA CTT CCA CCA CCA GCT CCT C (SEQ ID NO: 32), GAG CCC CGC ACT TCC ACC ACC AGC TCC T (SEQ ID NO: 33), CAT TGG AGC CCC GCA CTT CCA CCA CCA G (SEQ ID NO: 34), CCC GCA CTT CCA CCA CCA GCT CCT CCA TCT (SEQ ID NO: 35), TAG AAA GCG CCA TTG GAG CCC CGC ACT TCC (SEQ ID NO: 36), and AAG CGC CAT TGG AGC CCC GCA CTT CC (SEQ ID NO: 37).

G. Enhancers

In some embodiments, enhancers may be provided. The enhancers contribute to the success of reactions generating GC-rich product. A variety of enhancers may be included in PCR reactions in general to increase yield, specificity, and consistency, and may operate by lowering the Tm of template DNA. Enhancers may function through helix destabilization, neutralization of reaction inhibitors, or other mechanisms, including unknown mechanisms. Enhancers include, without limitation, betaine, betaine analogs, glycerol, bovine serum albumin (BSA), polyethylene glycol, tetramethylammonium chloride, 7-deaza-GTP, neutral detergents, dimethylsulfoxide (DMSO), methanol, ethanol, isopropanol, formamide, acetone, acetamide, N-methylformamide, N, N-dimethylformamide, acetone, acetimide, N-methylacetimide, N,N-dimethylacetimide, 2-pyrrolidone, N-methylpyrrolidone, propionamide, and isobutyramide. Neutral detergents include, without limitation, TWEEN-20, β-octyl-glucoside, Octyl-β-Thio-glucopyranoside, Triton X-100, Triton X-114, NP-40, Brij-35, Brij-58, Tween-80, Pluronic F-68, Pluronic F-127, Deoxy Big CHAP, CHAPS, CHES, nonyl phenoxylpolyethoxylethanol (Tergitol-type NP-40), and octyl phenoxylpolyethoxylethanol (Igepal CA-630). Betaine analogs include, without limitation, homodeanol betaine, deanol betaine, propio betaine, homoglycerol betaine, diethanol homobetaine, triethanol homobetaine, hydroxypropyl homobetaine, N-Methyl-N-(2-carboxyethyl)morpholinium inner salt, N-Methyl-N-(2-carboxyethyl)piperidinium inner salt, N-Methyl-N-(2-carboxyethyl)pyrrolidinium inner salt, N,N-dimethyl-N-(2-hydroxyethyl)-N-(2-sulfoethyl)ammonium inner salt, N,N-dimethyl-N-(2-hydroxyethyl)-N-(3-sulfopropyl)ammonium inner salt, N,N-dihydroxyethyl-N-methyl-N-(3-sulfopropyl)ammonium inner salt, N,N-dimethyl-N-(2-hydroxyethyl)-N-(4-sulfobutyl)ammonium inner salt, N-methyl-N-(3-sulfopropyl)morpholinium inner salt, and N-methyl-N-(3-sulfopropyl)piperidium inner salt.

Betaine, betaine analogs and/or other enhancers may be provided at molar concentrations between 0.01 and 5 M, 0.01 and 4 M, 0.01 and 3 M, 0.01 and 2.5 M, 0.02 and 5 M, 0.03 and 5 M, 0.04 and 5 M, 0.05 and 5 M, 0.07 and 5 M, 0.1 and 5 M, 0.2 and 5M, 0.3 and 5M, 0.4 and 5M, 0.5 and 5M, 0.7 and 5M, 1 and 5M, 1.5 and 5 M, 0.1 and 4 M, 0.5 and 3 M, 1 and 2.5 M, or 1.5 and 2.5 M, for example, about 0.01, 0.02, 0.05, 0.1, 0.2, 0.5, 0.75, 1, 1.25, 1.5, 1.6, 1.7, 1.8, 1.9, 2.0, 2.1, 2.2, 2.3, 2.4, 2.5, 3, 3.5, 4, 4.5, or 5 M. Alternatively, enhancers may be provided at w/v or v/v percentage concentrations of between 0.1 and 50%, 0.2 and 50%, 0.5 and 50%, 1 and 50%, 2 and 50%, 5 and 50%, 0.1 and 40%, 0.1 and 30%, 0.1 and 20%, 0.5 and 40%, 1 and 30%, or 2 and 20%, for example, about 0.1, 0.2, 0.5, 1, 2, 5, 10, 15, 20, 25, 30, 35, 40, 45, or 50% by volume. Neutral detergents may be provided at between 0.0001 and 10% by volume, 0.0002 and 10%, 0.0005 and 10%, 0.001 and 10%, 0.002 and 10%, 0.005 and 10%, 0.01 and 10%, 0.02 and 10%, 0.05 and 10%, 0.0001 and 5%, 0.0001 and 2%, 0.0001 and 1%, 0.0005 and 1%, or 0.001 and 1%, for example, about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, or 10% by volume. Those skilled in the art will recognize appropriate concentrations for various enhancers.

H. Magnesium Salt

The invention relates to methods comprising providing magnesium salts. A magnesium salt is a chemical compound containing magnesium and the conjugate base of an acid. The magnesium salts may comprise, for example and without limitation, magnesium chloride, magnesium acetate, magnesium sulfate, magnesium bromide, or magnesium iodide. The magnesium salts are provided in such quantity that the final concentration of magnesium may be between 1 and 5 mM, 1 and 4.5 mM, 1 and 4 mM, 1 and 3.5 mM, 1 and 3 mM, 1.5 and 5 mM, 2 and 5 mM, 2.5 and 5 mM, 3 and 5 mM, 1.5 and 4.5 mM, or 2 and 4 mM. For example, the final concentration of magnesium may be about 1, 1.5, 2, 2.5, 3, 3.5, 4, 4.5, or 5 mM.

I. Buffer

The invention relates to methods comprising providing buffers. The buffers may comprise, for example and without limitation, tris(hydroxymethyl)aminomethane (Tris), bis-tris propane, bicarbonate, phosphate, glycine, histidine, 4-(2-hydroxyethyl)-1-piperazineethanesulfonic acid (HEPES), 3-(N-morpholino)propanesulfonic acid (MOPS), and various conjugate bases/acids and salts thereof.

J. Data, Products, and Uses

In some embodiments, the products generated by the methods of the invention may comprise about 5, 10, 20, 30, 40, 50, 70, 100, 150, 200, 250, 300, 400, 500, 700, 800, 900, 1000, 2000 or more CGG repeats. In some embodiments, the amplification reactions of the invention involve amplifying alleles containing more repeats than the Coriell FMR1 5' UTR standards containing 20, 28-29, 118, 198, or about 330 CGG repeats. The products generated by the methods of the invention may comprise a number of CGG repeats between 5 and 2000, 10 and 2000, 20 and 2000, 30 and 2000, 40 and 2000, 50 and 2000, 70 and 2000, 100 and 2000, 150 and 2000, 200 and 2000, 250 and 2000, 300 and 2000, 5 and 1000, 5 and 700, 5 and 500, 5 and 400, 5 and 300, 10 and 1000, 10 and 700, 20 and 500, 30 and 400, or 100 and 300. The data obtained through the invention, the results of the tests, may be used to diagnose the presence or absence of a condition or disease. The data obtained through use of the invention may be used in determination of the genotype of an individual. The data obtained through the invention may be used to detect genotypes associated with Fragile X Syndrome, Fragile X-associated tremor ataxia syndrome, and Fragile X-associated primary ovarian insufficiency. Genetic loci associated with these conditions are known in the art and include without limitation FMR1, FMR2, the 5' UTR of FMR1, the 5' UTR of FMR2, the CGG repeats within the 5' UTR of FMR1, and the CGG repeats within the 5' UTR of FMR2. In an additional embodiment, the data obtained through the invention may be used to detect genotypes associated with GC-rich trinucleotide repeat disorders, such as Fragile X Syndrome, Fragile X-associated tremor ataxia syndrome, and Fragile X-associated primary ovarian insufficiency, myotonic dystrophy, Huntington's disease, spinobulbar muscular atrophy, Dentatorubropailidoluysian atrophy, and/or spinocerebellar ataxia. Genetic loci associated with these conditions are known in the art and include without limitation FMR1, FMR2, DMPK, ZNF9, HTT, AR, ATN1, ATXN1-3, ATXN7, ATXN10, CACNA1A, SCA8, PPP2R2B, and TBP. See, e.g., Nat Genet. 1996 May; 13(1): 105-8; Nat Genet. 1996 May; 13(1):109-13.

Example 1

The effect of varying GC/AT ratios, total dNTP concentration, and betaine concentration was measured by running a series of reactions with GC/AT ratios of 1, 5, or 10; total dNTP (Roche, GMP Grade Cat. No. G 04631129103, C 04631072103, A 04631056103, T 04631137103) concentrations of 0.75, 1.0, or 1.25 mM; and betaine (Sigma Cat. No. B0300-1VL) concentrations of 1.7, 2.0, or 2.2 M. The templates were a mixture of 10 ng each of the genomic DNAs shown in Table 1. Expand Long Template PCR System Buffer 2 (Roche Cat. No. 11681834001) was utilized along with recombinant Taq Polymerase (Roche, Cat. No. 03734935001) at 1.125 Units per reaction. The primers were as in Saluto et al, *J Mol Diagn* 7:605-12 (2005) at 1 µM for each primer. The PCR cycling profile was as in Saluto et al. except for the number of cycles, briefly outlined as follows: denaturation at 98° C. for 10 minutes; 10 cycles at 97° C. for 35 seconds, 64° C. for 35 seconds, 68° C. for 4 minutes; 15 cycles at 97° C. for 35 seconds, 64° C. for 35 seconds, 68° C. for 4 minutes, plus a 20-second increment for each cycle; and a final extension at 68° C. for 10 minutes. Six microliters of PCR product were electrophoresed at 5V/cm for 45 minutes on a 1.75% NuSieve Agarose gel with 1× Bionic Buffer followed by SYBR Gold staining and visualization by UV light.

TABLE 1

Genotypes of the Coriell genomic DNA Controls Tested

| Coriell ID | Gender | Phenotype | Genotype | CGG Triplet Repeat |
|---|---|---|---|---|
| NA20239A | Female | Clinically unaffected | Heterozygous: Normal/Full mutation | 20/198 |
| NA20233 | Male | Clinically unaffected | Pre mutation | 118 |
| NA07537 | Female | Clinically unaffected | Heterozygous: Normal/Full mutation | 28-29/>200 (~330) |

GC:AT Ratio, betaine concentration, and total dNTP concentration for lanes 1-3 and 5-28 are shown in Table 2.

TABLE 2

| Lane No. | GC:AT Ratio | [Betaine] | Total [dNTP] |
|---|---|---|---|
| 1 | 1:1 | 1.7 M | 0.75 mM |
| 2 | 5:1 | 1.7 M | 0.75 mM |
| 3 | 10:1 | 1.7 M | 0.75 mM |
| 5 | 1:1 | 2.0 M | 0.75 mM |

TABLE 2-continued

| Lane No. | GC:AT Ratio | [Betaine] | Total [dNTP] |
|---|---|---|---|
| 6 | 5:1 | 2.0 M | 0.75 mM |
| 7 | 10:1 | 2.0 M | 0.75 mM |
| 8 | 1:1 | 2.2 M | 0.75 mM |
| 9 | 5:1 | 2.2 M | 0.75 mM |
| 10 | 10:1 | 2.2 M | 0.75 mM |
| 11 | 1:1 | 1.7 M | 1.0 mM |
| 12 | 5:1 | 1.7 M | 1.0 mM |
| 13 | 10:1 | 1.7 M | 1.0 mM |
| 14 | 1:1 | 2.0 M | 1.0 mM |
| 15 | 5:1 | 2.0 M | 1.0 mM |
| 16 | 10:1 | 2.0 M | 1.0 mM |
| 17 | 1:1 | 2.2 M | 1.0 mM |
| 18 | 5:1 | 2.2 M | 1.0 mM |
| 19 | 10:1 | 2.2 M | 1.0 mM |
| 20 | 1:1 | 1.7 M | 1.25 mM |
| 21 | 5:1 | 1.7 M | 1.25 mM |
| 22 | 10:1 | 1.7 M | 1.25 mM |
| 23 | 1:1 | 2.0 M | 1.25 mM |
| 24 | 5:1 | 2.0 M | 1.25 mM |
| 25 | 10:1 | 2.0 M | 1.25 mM |
| 26 | 1:1 | 2.2 M | 1.25 mM |
| 27 | 5:1 | 2.2 M | 1.25 mM |
| 28 | 10:1 | 2.2 M | 1.25 mM |

Amplification of the alleles with higher numbers of CGG repeats was clearly improved at higher betaine concentrations and GC/AT ratios (FIG. 1).

Example 2

Figure 2:
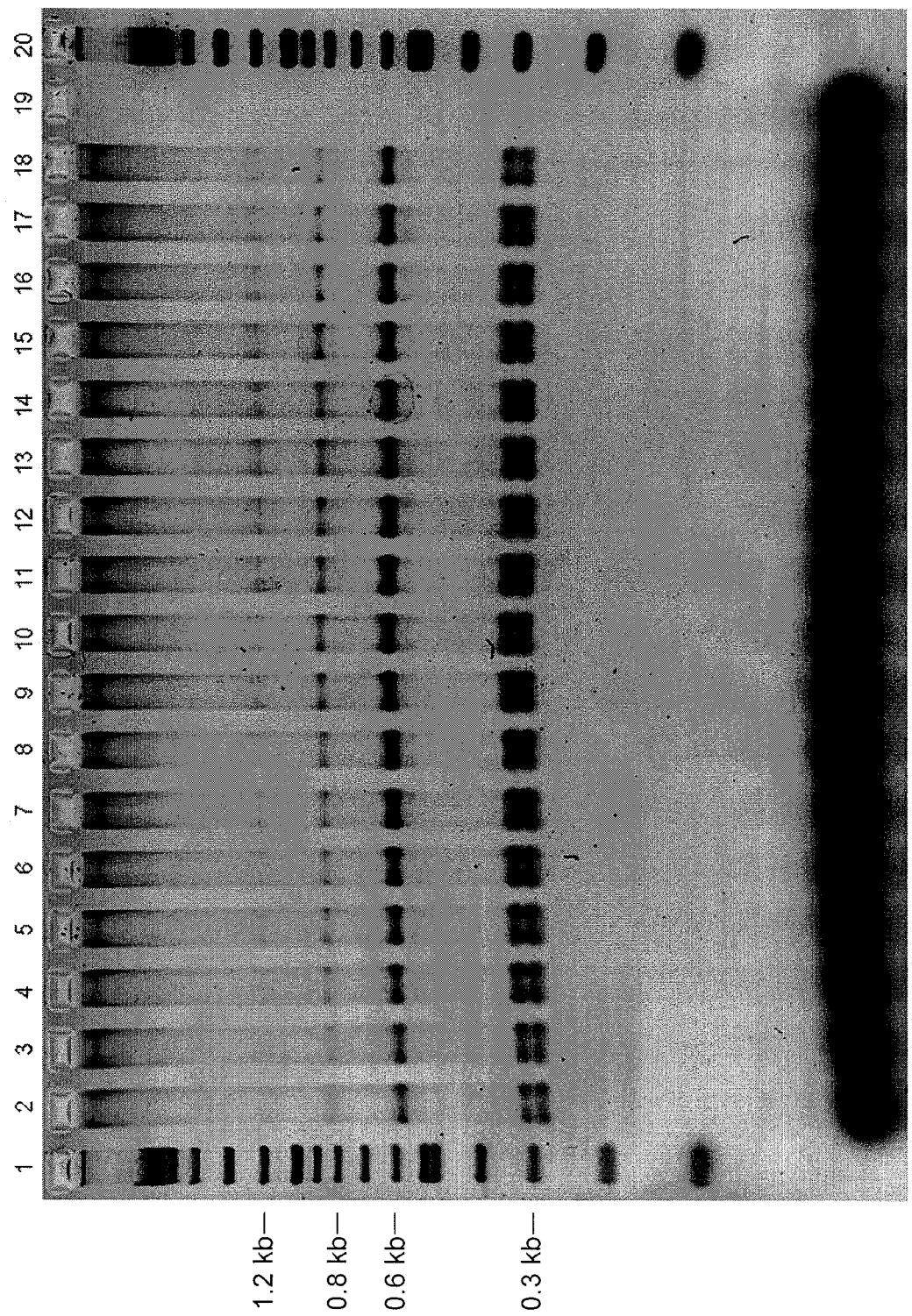
FIG. 2 is a photograph of a SYBR-Gold stained gel. Lane 1 and lane 20 are size markers, and sizes of selected bands are indicated to the left of lane 1. Lane 2 contains the product of a PCR reaction using a 1:1 GC/AT ratio of dNTPs. Lanes 3-18 show products of PCR reactions with GC/AT ratios of dNTPs increasingly biased toward G and C. Lane 19 contains the product of a no template control PCR reaction using a 1:1 GC/AT ratio of dNTPs.

To further test the effect of biased GC/AT dNTP ratios, a set of PCR reactions was run using different degrees of bias with ratios from 1.1 to 25 (FIG. 2), plus a control reaction with a GC/AT ratio of 1. Total dNTP (Roche, GMP Grade Cat. No. G 04631129103, C 04631072103, A 04631056103, T 04631137103) concentration was held constant at 1 mM. A mixture of templates, totaling 10 ng, containing fragments of alleles of the 5' UTR of FMR1 having 20, 28, 118, 198, and 336 CGG repeats was provided. Expand Long Template PCR System Buffer 2 (Roche Cat. No. 11681834001) was utilized along with recombinant Taq Polymerase (Roche, Cat. No. 03734935001) at 1.125 Units per reaction. Betaine (Sigma Cat. No. B0300-1VL) was present at 2.2 M. The primers were as in Saluto et al, *J Mol Diagn* 7:605-12 (2005) at 1 µM for each primer. The PCR cycling profile was as in Saluto et al. except for the number of cycles, briefly outlined as follows: denaturation at 98° C. for 10 minutes; 10 cycles at 97° C. for 35 seconds, 64° C. for 35 seconds, 68° C. for 4 minutes; 15 cycles at 97° C. for 35 seconds, 64° C. for 35 seconds, 68° C. for 4 minutes, plus a 20-second increment for each cycle; and a final extension at 68° C. for 10 minutes. Six microliters of PCR product were electrophoresed at 5 V/cm for 45 minutes on a 2.0% NuSieve Agarose gel with 1× Bionic Buffer followed by SYBR Gold staining and visualization by UV light.

GC:AT ratios for lanes 2-18 are shown in Table 3.

TABLE 3

GC:AT ratios

| Lane No. | GC:AT Ratio |
|---|---|
| 2 | 1:1 |
| 3 | 1.1:1 |
| 4 | 1.2:1 |
| 5 | 1.4:1 |
| 6 | 1.6:1 |

TABLE 3-continued

GC:AT ratios

| Lane No. | GC:AT Ratio |
|---|---|
| 7 | 1.8:1 |
| 8 | 2:1 |
| 9 | 2.5:1 |
| 10 | 3:1 |
| 11 | 3.5:1 |
| 12 | 4:1 |
| 13 | 4.5:1 |
| 14 | 5:1 |
| 15 | 10:1 |
| 16 | 15:1 |
| 17 | 20:1 |
| 18 | 25:1 |

Synthesis and yield of higher molecular weight products, containing higher numbers of CGG repeats and a higher overall GC-richness, was clearly improved relative to lane 1 over a broad range of GC/AT ratios.

The specification is most thoroughly understood in light of the teachings of the references cited within the specification. The embodiments within the specification provide an illustration of embodiments of the invention and should not be construed to limit the scope of the invention. The skilled artisan readily recognizes that many other embodiments are encompassed by the invention. All publications and patents cited in this disclosure are incorporated by reference in their entirety. To the extent the material incorporated by reference contradicts or is inconsistent with this specification, the specification will supersede any such material. The citation of any references herein is not an admission that such references are prior art to the present invention.

Unless otherwise indicated, all numbers expressing quantities of ingredients, reaction conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

What is claimed is:

1. A method of increasing the processivity of one or more DNA polymerases on at least one GC-rich DNA template having a GC-richness of at least 51%, the method comprising performing a DNA amplification reaction in an aqueous solution comprising the at least one GC-rich DNA template having a GC-richness of at least 51%; at least two distinct primers; at least one enhancer; and dNTPs in a GC/AT ratio of 1.2 or higher.

2. The method of claim 1, wherein the GC/AT ratio is between 1.4 and 25.

3. The method of claim 1, wherein the GC/AT ratio is between 2.5 and 10.

4. The method of claim 1, in which the GC-rich DNA template has a GC-richness of at least 65%.

5. The method of claim 1, in which the GC-rich DNA template has a GC-richness of at least 90%.

6. The method of claim 1, in which the GC-rich DNA template comprises at least five consecutive repeats of a di-, tri-, or tetranucleotide consisting of G and C residues.

7. The method of claim 1, in which the GC-rich DNA template comprises at least part of the 5' UTR of FMR1.

8. The method of claim 1, in which the GC-rich DNA template comprises CGG repeats of the 5' UTR of FMR1.

9. The method of claim 1, in which the GC-rich DNA template comprises at least part of the 5' UTR of FMR2.

10. The method of claim 1, in which the GC-rich DNA template comprises CGG repeats of the 5' UTR of FMR2.

11. A method of increasing the processivity of one or more DNA polymerases on at least one GC-rich DNA template, the method comprising performing a DNA amplification reaction in an aqueous solution comprising the at least one GC-rich DNA template; dNTPs in a GC/AT ratio of 1.2 or higher; and at least one enhancer from each of (a) and (b):
   a. a first enhancer, which is betaine or a betaine analog; and
   b. at least one additional enhancer selected from the group consisting of DMSO, a neutral detergent, and 7-deaza-GTP.

12. The method of claim 1, comprising amplifying the GC-rich template in an aqueous solution comprising
   a. the at least one GC-rich DNA template;
   b. at least one magnesium salt;
   c. at least one DNA polymerase;
   d. at least one buffer;
   e. dNTPs in a GC/AT ratio of 1.2 or higher; and
   f. the at least one enhancer,
   and subjecting the solution to at least one incubation period during which amplification occurs.

13. The method of claim 12, wherein the at least one enhancer comprises at least one of betaine, a betaine analog, 7-deaza-GTP, DMSO, and a neutral detergent.

14. The method of claim 1, in which the at least one GC-rich template is amplified by a procedure chosen from at least one of SDA, NASBA, LAMP, and LCR.

15. The method of claim 1, in which at least one primer anneals to the at least one GC-rich template.

16. A method of increasing the processivity of one or more DNA polymerases on at least one GC-rich DNA template comprising CGG repeats of the 5' UTR of FMR1, the method comprising amplifying the template comprising CGG repeats of the 5' UTR of FMR1 by PCR in an aqueous solution comprising:
   a. dNTPs in a GC/AT ratio between 2 and 10;
   b. at least one enhancer chosen from betaine, DMSO, and a neutral detergent;
   c. at least one DNA polymerase;
   d. a total magnesium concentration of 1.5-2 mM; and
   e. a total dNTP concentration of 0.7-0.9 mM.

17. The method of claim 16, in which the neutral detergent comprises TWEEN-20.

18. The method of claim 16, in which the PCR produces product comprising at least 200 CGG repeats.

19. The method of claim 16, in which the PCR produces product comprising at least 300 CGG repeats.

20. A method of detecting a genotype associated with a GC-rich trinucleotide repeat disorder, comprising performing a DNA amplification reaction using at least two distinct primers on at least one genotype associated with the GC-rich trinucleotide repeat disorder, in which the processivity of one or more DNA polymerases is increased by providing an aqueous solution comprising dNTPs in a GC/AT ratio of 1.2 or higher.

21. A method of detecting a genotype associated with Fragile X Syndrome, Fragile X-associated tremor ataxia syndrome, and/or Fragile X-associated primary ovarian insufficiency, comprising performing a DNA amplification reaction using at least two distinct primers on at least one GC-rich DNA template associated with Fragile X Syndrome, Fragile X-associated tremor ataxia syndrome, and/or Fragile X-associated primary ovarian insufficiency, in which the processivity of one or more DNA polymerases is increased by providing an aqueous solution comprising dNTPs in a GC/AT ratio of 1.2 or higher.

22. The method of claim 21, wherein the template comprises CGG repeats of the 5' UTR of FMR1 or FMR2.

23. The method of claim 21, wherein the GC/AT ratio is between 1.4 and 25.

24. The method of claim 21, wherein the GC/AT ratio is between 2 and 10.

25. The method of claim 21, wherein the aqueous solution further comprises at least one enhancer.

26. The method of claim 20, in which the aqueous solution further comprises at least one enhancer.

27. The method of claim 26, in which the at least one enhancer comprises at least one of betaine, a betaine analog, DMSO, or a neutral detergent.

* * * * *